United States Patent
Zhang et al.

(10) Patent No.: US 12,305,216 B2
(45) Date of Patent: May 20, 2025

(54) METHOD FOR SELECTING AEROBIC DENITRIFYING FUNGUS AND METHOD FOR REMEDIATING WATER BODY WITH LOW CARBON-TO-NITROGEN RATIO USING AEROBIC DENITRIFYING FUNGUS

(71) Applicant: XI'AN UNIVERSITY OF ARCHITECTURE AND TECHNOLOGY, Xi'an (CN)

(72) Inventors: Haihan Zhang, Xi'an (CN); Ben Ma, Xi'an (CN); Limin Niu, Xi'an (CN)

(73) Assignee: XI'AN UNIVERSITY OF ARCHITECTURE AND TECHNOLOGY, Xi'an (CN)

( * ) Notice: Subject to any disclaimer, the term of this patent is extended or adjusted under 35 U.S.C. 154(b) by 0 days.

(21) Appl. No.: 18/735,209

(22) Filed: Jun. 6, 2024

(65) Prior Publication Data
US 2024/0309421 A1  Sep. 19, 2024

Related U.S. Application Data

(63) Continuation of application No. PCT/CN2023/132745, filed on Nov. 20, 2023.

(30) Foreign Application Priority Data

Feb. 24, 2023 (CN) .......................... 202310160552.8

(51) Int. Cl.
| | | |
|---|---|---|
| C12Q 1/04 | (2006.01) | |
| C02F 3/34 | (2023.01) | |
| C02F 101/38 | (2006.01) | |
| C12N 1/14 | (2006.01) | |
| C12Q 1/24 | (2006.01) | |
| C12Q 1/6895 | (2018.01) | |
| C12R 1/885 | (2006.01) | |

(52) U.S. Cl.
CPC .............. *C12Q 1/045* (2013.01); *C02F 3/347* (2013.01); *C12N 1/145* (2021.05); *C12Q 1/24* (2013.01); *C12Q 1/6895* (2013.01); *C02F 2101/38* (2013.01); *C12R 2001/885* (2021.05)

(58) Field of Classification Search
None
See application file for complete search history.

(56) References Cited

FOREIGN PATENT DOCUMENTS

| CN | 101434905 A | 5/2009 |
| CN | 103484378 A | 1/2014 |
| CN | 103571759 A | 2/2014 |
| CN | 109810923 A | 5/2019 |
| CN | 110484458 A | 11/2019 |
| CN | 116162550 A | 5/2023 |

OTHER PUBLICATIONS

Zhang, Haihan, et al. "Nitrogen removal by mix-cultured aerobic denitrifying bacteria isolated by ultrasound: performance, co-occurrence pattern and wastewater treatment." Chemical Engineering Journal 372 (2019): 26-36. (Year: 2019).*
Ogaki, Mayara B., et al. "Diversity and bioprospecting of cultivable fungal assemblages in sediments of lakes in the Antarctic Peninsula." Fungal Biology 124.6 (2020): 601-611. (Year: 2020).*
DRBC Agar Technical Sheet (2014); available online at: https://www.liofilchem.net/login/pd/ts/610237_TS.pdf (Year: 2014).*
Haihan Zhang, et al., Biological nitrogen removal and metabolic characteristics of a novel aerobic denitrifying fungus *Hanseniaspora uvarum* strain KPL108, Bioresource Technology, 2018, pp. 569-577, vol. 267.
Haihan Zhang, et al., Nitrogen reduction by aerobic denitrifying fungi isolated from reservoirs using biodegradation materials for electron donor: Capability and adaptability in the lower C/N raw water treatment, Science of the Total Environment, 2023, pp. 1-12, vol. 864, 161064.
Shi Yinjie, Nitrogen Removal Performance and Community Composition of the Aerobic Denitrifying Bacteria in Reservoirs, Xi'an University of Architecture and Technology, 2022, pp. 1-88.
Kang Peng-Liang, et al., Community Structure and Denitrification Characteristics of Aerobic Denitrifiers in Lake and Reservoir, Xi'an University of Architecture and Technology, 2018, pp. 1-70.
Kang Peng-Liang, et al.,Denitrification Characteristics and Community Structure of Aerobic Denitrifiers from Lake and Reservoir Sediments, Environmental Science, 2018, pp. 2431-2437, vol. 39 No. 5.
Guo Shao-Peng, et al., Isolation and Screening of High-Efficiency Nitrification and Denitrification Functional Strains and Effect Evaluation, Oceanologia Et Limnologia Sinica, 2020, pp. 1520-1529, vol. 51 No. 6.

* cited by examiner

*Primary Examiner* — Robert J Yamasaki
(74) *Attorney, Agent, or Firm* — Bayramoglu Law Offices LLC

(57) ABSTRACT

A method for isolating and selecting *Trichoderma Virens* with an aerobic denitrification function and a method for remediating a water body with a low carbon-to-nitrogen ratio using the *Trichoderma Virens* are provided. Compared with the prior art, the biological treatment adopted by the present disclosure can allow the relatively-complete removal of nitrates without producing a residue, and exhibits advantages such as low cost, efficiency, and eco-friendliness. Further, the biological treatment adopted by the present disclosure can enhance the resistance of the fungus to toxic compounds and harsh environments, significantly promote the removal of nitrogen and organic matters in a water body, improve a decontamination ability of a water body, and increase the diversity of microorganisms in a water body, thereby accelerating the promotion of remediation of a water quality of a water body with a low carbon-to-nitrogen ratio. Therefore, the present disclosure has an extensive application potential.

4 Claims, 4 Drawing Sheets
Specification includes a Sequence Listing.

SEQUENCE LISTING

```
Sequence total quantity: 1
SEQ ID NO: 1            moltype = DNA   length = 509
FEATURE                 Location/Qualifiers
source                  1..509
                        mol_type = other DNA
                        organism = Trichoderma Virens
SEQUENCE: 1
atccgaggtc acatttcaga agtttggggt gtttaacggc tgtggacgcc gcgctcccga   60
tgcgagtgtg caaactactg cgcaggagag gctgcggcga gaccgccact gtatttcggg  120
gccggccccg taaagggccg atccccaacg ccgaccccc ggaggggttc cagggttgaa  180
atgacgctcg gacaggcatg cccgccagaa tactggcggg cgcaatgtgc gttcaaagat  240
tcgatgattc actgaattct gcaattcaca ttacttatcg catttcgctg cgttcttcat  300
cgatgccaga accaagagat ccgttgttga aagtttttgat tcattttcga aacgcccacg  360
aggggcgccg agatggctca gatagtaaaa aacccgcgag ggggtataca ataagagttt  420
tggttggtcc tccggcgggc gccttggtcc ggggctgcga cgcacccggg gcagagatcc  480
cgccgaggca acagtttggt aacgttcac                                    509
```

METHOD FOR SELECTING AEROBIC DENITRIFYING FUNGUS AND METHOD FOR REMEDIATING WATER BODY WITH LOW CARBON-TO-NITROGEN RATIO USING AEROBIC DENITRIFYING FUNGUS

CROSS REFERENCE TO THE RELATED APPLICATIONS

This application is a continuation application of International Application No. PCT/CN2023/132745, filed on Nov. 20, 2023, which is based upon and claims priority to Chinese Patent Application No. 202310160552.8, filed on Feb. 24, 2023, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBZYHH002-PKG_Sequence_Listing.xml, created on May 7, 2024, and is 2,367 bytes in size. Trichoderma virens strain D4 is deposited on Mar. 10, 2025, with the China Center for Type Culture Collection (CCTCC) in accordance with the Budapest Treaty On The International Recognition Of The Deposit Of Microorganisms For The Purpose Of Patent Procedure. The deposit can be access on CCTCC M 2025399.

TECHNICAL FIELD

The present disclosure belongs to the technical field of selection and application of microorganisms, and specifically relates to a method for isolating and selecting *Trichoderma Virens* with an aerobic denitrification function and a method for remediating a water body with a low carbon-to-nitrogen ratio using the *Trichoderma Virens*.

BACKGROUND

Drinking water reservoirs play an important role in the supply of drinking water for residents. Nitrogen oxides in the air, after falling with rainwater, will react with salts in the soil to produce nitrates, and excessive nitrates in the reservoir water body will cause the eutrophication of the water body and make algae undergo over-growth to seriously affect an aquatic ecosystem of the reservoir. More importantly, nitrates can be converted into nitrites under specified conditions, and after entering the human body, nitrites can destroy hemoglobin to affect the human health. The regulation and management of the drinking water reservoirs is listed as the first barrier for safety of drinking water, and water qualities of the drinking water reservoirs are directly related to the safety of urban drinking water and are a major issue related to the national welfare and the people's livelihood. Therefore, how to remove the nitrogen pollution in the drinking water reservoirs and ensure the safety of drinking water supply has become an important issue that is widely concerned and urgent to be solved.

Currently, the most common treatment methods for removing nitrates include the ion exchange method, the adsorption method, the electrochemical method, the reverse osmosis method, the chemical method, and the biological method. The biological treatment can completely remove nitrates without producing residues, and has advantages such as low cost, efficiency, and eco-friendliness. In drinking water reservoirs, in order to prevent the occurrence of an anaerobic environment in a water body at the bottom of a reservoir during the thermal stratification period and reduce the endogenous release from bottom sediments, artificial mixing and oxygenation technologies have been widely used in many drinking water reservoirs. Due to the use of artificial mixing and oxygenation technologies, aerobic conditions are maintained in drinking water reservoirs. In addition, the carbon-to-nitrogen ratio in drinking water reservoirs is at a low level (C/N=1 to 3, and N=1 mg/L to 3 mg/L), such that microorganisms cannot grow well. Because the carbon-to-nitrogen ratio in drinking water reservoirs cannot be increased by additionally adding an organic carbon source, such as methanol and an acetate, under these conditions, oligotrophic aerobic denitrifying microorganisms can provide a novel solution for in situ remediation of drinking water reservoirs. Therefore, it is urgent to select aerobic denitrifying microorganisms that can adapt to a low carbon-to-nitrogen ratio and have a high denitrification efficiency.

SUMMARY

In order to solve the problems existing in the background, a first objective of the present disclosure is to provide a method for isolating and selecting an aerobic denitrifying fungus that can be suitable for a denitrification treatment of a water body with a low carbon-to-nitrogen ratio, and a second objective of the present disclosure is to provide a practical use of the aerobic denitrifying fungus in remediation of a water body with a low carbon-to-nitrogen ratio.

In order to allow the above objectives, the present disclosure provides the following technical solutions:

A method for selecting an aerobic denitrifying fungus is provided, including: treating sediments in a reservoir by an ultrasonic shaking technology, isolating and purifying fungal strains, and selecting a fungus with an efficient aerobic denitrification function using a denitrification medium.

Further, the method includes the following steps:

S1, subjecting a mud/water mixture collected from a drinking water reservoir to an ultrasonic treatment to obtain a suspension; S2, diluting the suspension to obtain a diluted suspension;

S3, coating the diluted suspension on a fungal solid medium to produce colonies;

S4, picking fungal colonies with different shapes, colors, and characteristics from the fungal solid medium; streaking the fungal colonies on a fungal solid medium, and incubating a streaked fungal solid medium in a biochemical incubator to produce colonies; and repeating the above streaking process multiple times until pure colonies are obtained;

S5, screening the pure colonies in a denitrification medium;

S6, selecting a fungus with an optimal aerobic denitrification ability; and

S7, identifying the fungal strain by a gene sequencing technology, and naming an identified fungal strain as *Trichoderma Virens* D4, where an internal transcribed spacer (ITS) sequence for the fungal strain (SEQ ID NO: 1) is specifically as follows:

```
ATCCGAGGTCACATTTCAGAAGTTTGGGGTGTTTAACGGCTGTGG

ACGCCGCGCTCCCGATGCGAGTGTGC\AAACTACTGCGCAGGAGA

GGCTGCGGCGAGACCGCCACTGTATTTCGGGGCCGGCCCCGTAAA
```

-continued
```
GGGCCGATCC\CCAACGCCGACCCCCGGAGGGGTTCCAGGGTTG

AAATGACGCTCGGACAGGCATGCCCGCCAGAATACTGGC\GGGCG

CAATGTGCGTTCAAAGATTCGATGATTCACTGAATTCTGCAATTC

ACATTACTTATCGCATTTCGCTGCG\TTCTTCATCGATGCCAGAA

CCAAGAGATCCGTTGTTGAAAGTTTTGATTCATTTTCGAAACGCC

CACGAGGGGC\GCCGAGATGGCTCAGATAGTAAAAAACCCGCGAG

GGGGTATACAATAAGAGTTTTGGTTGGTCCTCCGGCGGG\CGCCT

TGGTCCGGGGCTGCGACGCACCCGGGGCAGAGATCCCGCCGAGGC

AACAGTTTGGTAACGTTCAC.
```

Preferably, a method for remediating a water body with a low carbon-to-nitrogen ratio using an aerobic denitrifying fungus is provided, including: inoculating the aerobic denitrifying fungus selected above into the water body with the low carbon-to-nitrogen ratio, where the water body includes an urban river or a lake or a reservoir to allow remediation of the water body with the low carbon-to-nitrogen ratio.

The present disclosure has the following beneficial effects:

(1) Compared with the most common treatment methods for nitrate removal in the prior art, such as an ion exchange method, an adsorption method, an electrochemical method, a reverse osmosis method, and a chemical method, the biological treatment adopted by the present disclosure can allow the relatively-complete removal of nitrates without producing a residue, and has advantages such as low cost, efficiency, and eco-friendliness.

(2) Compared with bacteria, the fungus selected by the present disclosure can secrete a large number of enzymes, which facilitates the strong decomposition of organics. Further, spores of the fungus have complicated cell walls, which can enhance the resistance of the fungus to toxic compounds and harsh environments.

(3) The present disclosure introduces a novel biotechnology where sediments in a reservoir are treated with an ultrasonic shaking technology, fungal strains are further isolated and purified, and a fungus with an efficient aerobic denitrification function is selected with a denitrification medium. The fungus selected is suitable for the remediation of a water body with a low carbon-to-nitrogen ratio such as lakes and reservoirs, and can significantly promote the removal of nitrogen and organic matters in a water body, improve a decontamination ability of a water body, and increase the diversity of microorganisms in a water body, thereby accelerating the promotion of remediation of a water quality of a water body with a low carbon-to-nitrogen ratio.

(4) As a bioremediation technology, the present disclosure is eco-friendly, will not cause a harm and pollution to a native environment of a water body, and has an extensive application potential.

DETAILED DESCRIPTION OF THE EMBODIMENTS

The technical solutions of the present disclosure are further described in detail below in conjunction with specific embodiments, but the protection scope of the present disclosure is not limited to the following description.

A method for selecting an aerobic denitrifying fungus is provided, including: sediments in a reservoir are treated by an ultrasonic shaking technology, fungal strains are isolated and purified, and a fungus with an efficient aerobic denitrification function is selected using a denitrification medium.

Further, the method includes the following steps:

S1, A mud/water mixture is collected from a drinking water reservoir through sediment screening and separation and treated for 10 s by an ultrasonic machine KQ-500DE with a power 40% of a rated power to obtain a suspension, where the rated power is 500 w.

S2, 5 mL of the suspension is taken and diluted by a 10-fold serial dilution method to $10^{-1}$, $10^{-2}$, and $10^{31\ 3}$.

S3, 100 µL of each diluted suspension is taken and coated on a fungal solid medium with 3 replicates for each diluted suspension, and an inoculated fungal solid medium is incubated in a biochemical incubator at 30° C. for 5 d to 7 d until colonies are formed.

S4, Fungal colonies with different shapes, colors, and characteristics are picked from the fungal solid medium and streaked on a fungal solid medium, and a streaked fungal solid medium is incubated in a biochemical incubator to produce colonies; and the above streaking process is repeated multiple times until pure colonies are obtained.

S5, The pure colonies are screened in a denitrification medium. Preferably, The pure colonies are picked by an inoculation needle and inoculated into a 250 ml Erlenmeyer flask with 150 mL of a DM medium, or colonies growing on a plate are washed with phosphate buffer and then screened in a DM medium. The pure colonies are cultivated on a shaker (30° C., 120 r/min) for 2 d to obtain a seed solution for storage. At 24 h and 48 h, a sample is collected, tested for a fungal density ($OD_{600}$), and then filtered through a 0.45 um filter membrane, and a resulting filtrate is tested for concentrations of nitrate nitrogen ($NO_3$—N) and total nitrogen (TN). After the 2 d cultivation, a resulting fungal solution (in a logarithmic phase) is mixed with a 50% glycerol solution in a ratio of 1:1, and a resulting mixed solution is placed in a sterilized 10 mL centrifuge tube in a sealed state and stored (−80° C. freezer) for later use. Through the above screening, a fungus with an optimal aerobic denitrification ability can be obtained. A single fungus with a high $NO_3$—Nremoval efficiency is selected and cultivated in DM for further research.

S6, A fungus with an optimal aerobic denitrification ability is selected.

Figure 1:
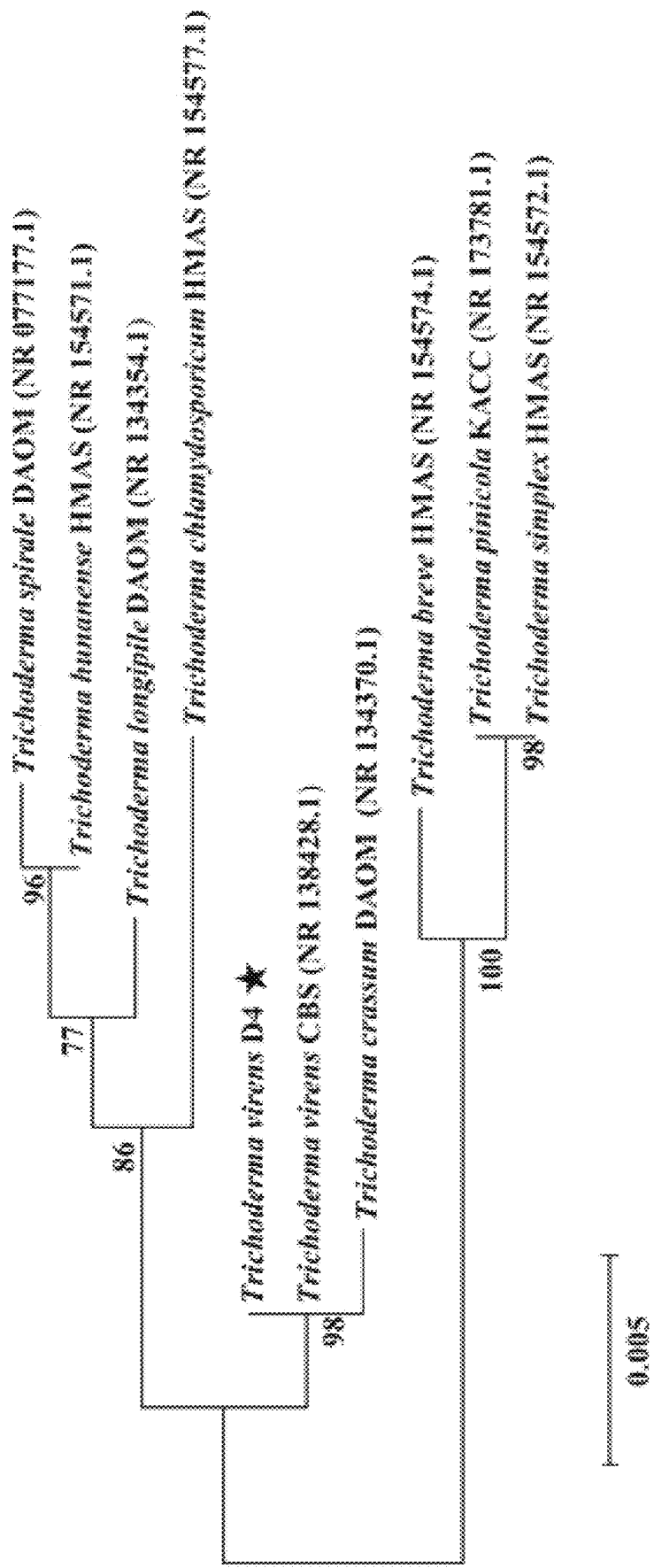
FIG. 1 shows a growth and development tree pattern of the aerobic denitrifying fungus Trichoderma Virens D4 in the present disclosure.

S7, The fungal strain is identified by a gene sequencing technology. Preferably, the fungal strain is identified by an ITS gene sequencing technology. DNA is extracted with a DNA isolation kit according to instructions of a manufacturer. An ITS gene is amplified with primers ITS1 and ITS4. A PCR product of the ITS gene is subjected to Sanger sequencing and purification with an ABI3730-XL sequencer (USA). The ITS sequence is stored in the National Center for Biotechnology Information (NCBI) database with an accession number OK560679. Sequence results of the strain are uploaded to the database through MEGA (version 5.05) and compared with the existing fungal ITS gene sequences in the database. A phylogenetic tree is constructed, the genetic characteristics of the strain are analyzed, and the species and genetic evolutionary status of the strain are determined. Results are shown in FIG. 1. The fungal strain identified is named *Trichoderma Virens* D4, and an ITS sequence for the fungal strain (SEQ ID NO: 1) is specifically as follows:

```
ATCCGAGGTCACATTTCAGAAGTTTGGGGTGTTTAACGGCTGTGG

ACGCCGCGCTCCCGATGCGAGTGTGC\AAACTACTGCGCAGGAGA

GGCTGCGGCGAGACCGCCACTGTATTTCGGGGCCGGCCCCGTAAA

GGGCCGATCC\CCAACGCCGACCCCCCGGAGGGGTTCCAGGGTTG

AAATGACGCTCGGACAGGCATGCCCGCCAGAATACTGGC\GGGCG

CAATGTGCGTTCAAAGATTCGATGATTCACTGAATTCTGCAATTC

ACATTACTTATCGCATTTCGCTGCG\TTCTTCATCGATGCCAGAA

CCAAGAGATCCGTTGTTGAAAGTTTTGATTCATTTTCGAAACGCC

CACGAGGGGC\GCCGAGATGGCTCAGATAGTAAAAAACCCGCGAG

GGGGTATACAATAAGAGTTTTGGTTGGTCCTCCGGCGGG\CGCCT

TGGTCCGGGGCTGCGACGCACCCGGGGCAGAGATCCCGCCGAGGC

AACAGTTTGGTAACGTTCAC.
```

A fungus with an optimal aerobic denitrification ability can be selected and identified through the above steps of the present disclosure.

Further, a method for selecting an aerobic denitrifying fungus is provided, including: the aerobic denitrifying fungus selected above is inoculated into a water body with a low carbon-to-nitrogen ratio such as an urban river or a lake or a reservoir to allow remediation of the water body with the low carbon-to-nitrogen ratio.

The following experimental contents are intended to provide the verification and practical application of a denitrification ability of the aerobic denitrifying fungus *Trichoderma Virens* D4 in a water body with a low carbon-to-nitrogen ratio.

The strain *Trichoderma Virens* D4 (10% v/v) is inoculated in a 250 ml Erlenmeyer flask with 150 mL of a DM medium and cultivated in a shaking incubator for 48 h (30° C. and 125 r/min), during which a sample is collected every 3 h and tested for a fungal density ($OD_{600}$) and a concentration of dissolved organic carbon (DOC) to estimate characteristics of cell propagation and a reduction efficiency of DOC. A mixed culture is collected and tested for $OD_{600}$ and DOC every 3 h until 72 h. These experiments are conducted three times (n=3).

10 mL of the culture of the strain is inoculated into a DM medium (150 mL) and cultivated in a dark incubator at 30° C. and 125 r/min. In order to investigate the aerobic denitrification ability of the strain, a shake flask test is conducted in a DM liquid medium with $KNO_3$ as the only nitrogen source. During a cultivation process, a culture is collected periodically (every 3 h) using a sterilized pipette (Eppendorf, Germany), then centrifuged at 8,000 r/min for 10 min, and filtered through a 0.45 μm filter membrane, and a resulting supernatant is collected and tested for concentrations of nitrate nitrogen ($NO_3$—N), nitrous nitrogen ($NO_2$—N), ammonia nitrogen ($NH_{4^+}$—N), and TN. Three parallel samples are measured each time (n=3).

Figure 2:
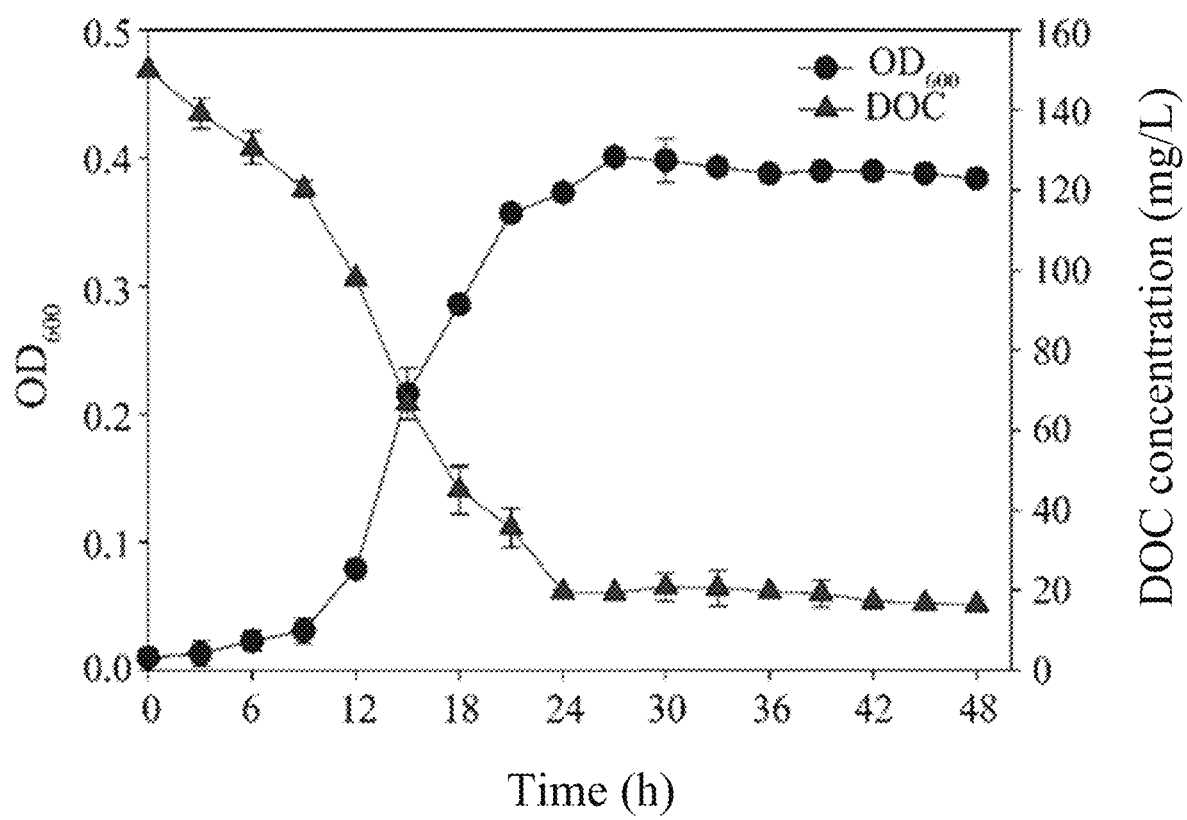
FIG. 2 shows a growth curve and a decarburization characteristic curve of the aerobic denitrifying fungus Trichoderma Virens D4 in the present disclosure.

Experiment 1: The strain (10 mL) was added to 140 mL of DM with 15 mg/L $KNO_3$ as the only nitrogen source (C/N =10) and subjected to a 48 h shaker test. FIG. 2 shows the growth and DOC removal performance of the strain. During a 0 h to 9 h adaptation phase after the strain was inoculated, a concentration of the strain increased slowly from 0.01 to 0.031. At 12 h to 27 h, an OD value of the strain rapidly increased to 0.079 and the strain entered a logarithmic phase. At 27 h to 42 h, OD600 reached a maximum value of 0.401 and then tended to be stable, that is, a growth curve tended to be smooth and an OD600 value did not change significantly, indicating that the cultivation of the strain entered a quiescent state. With the further extension of a cultivation time (45 h to 48 h), an $OD_{600}$ value was inversely proportional to the cultivation time, a death phase was reached, and a fungal density also decreased slightly.

A polynomial equation for a proliferation curve of the strain is as follows:

$y=-0.000007$ $x^3+0.0002$ $x^2+0.0143$ $x-0.0392$ ($R^2=0.9309$)

Organic matters are an important source for energy and electron donors to maintain the reproduction and denitrification processes of microorganisms. As shown in FIG. 2, there is a negative correlation between the fungal growth and the DOC concentration. During a proliferation process, a DOC concentration in DM decreases significantly under aerobic conditions, especially in a logarithmic phase of the strain. At 27 h, the DOC concentration decreases from 150 mg/L to 19.34 mg/L, indicating a removal rate of 87.11%. At 48 h, the DOC concentration is 16.34 mg/L, indicating a maximum removal rate of 89.11%. These results show that the aerobic denitrifying fungus *Trichoderma Virens* D4 can well utilize DOC during growth, indicating that it is feasible to remove the carbon pollution with the strain.

Experiment 2: Denitrification performance of the aerobic denitrifying fungus *Trichoderma Virens* D4

Figure 3:
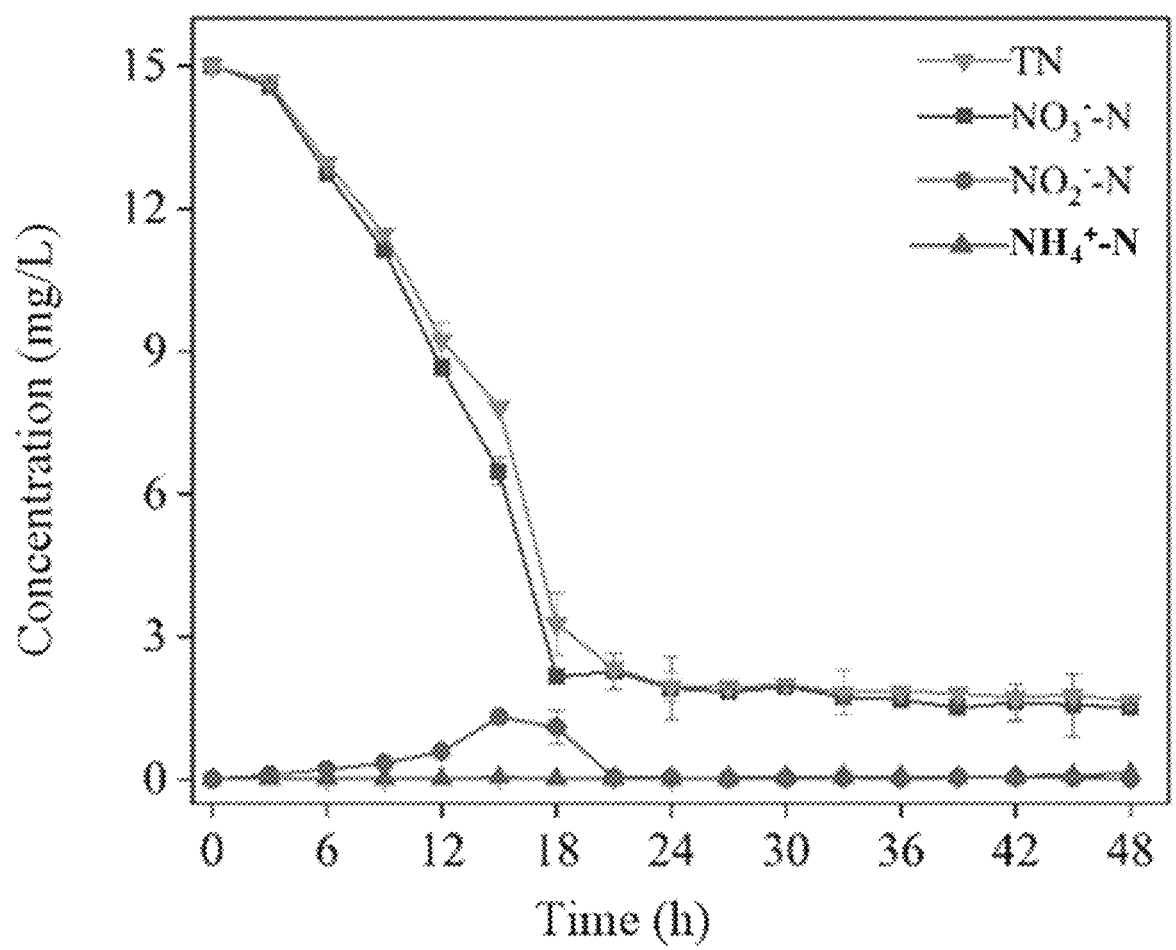
FIG. 3 shows denitrification characteristic curves of the aerobic denitrifying fungus Trichoderma Virens D4 in the present disclosure.

The strain *Trichoderma Virens* D4 was cultivated for 48 h with NO3-N as the only nitrogen source. During the cultivation, a change law of denitrification performance is shown in FIG. 3: At 6 h, the removal of $NO_3$—N starts, and an accumulated amount of $NO_3$—N decreases from the initial 15 mg/L to 12.74 mg/L, indicating a removal rate of 15.05%. In a logarithmic phase, concentrations of TN and NO3 -- N decrease extremely. At 27 h, a concentration of NO3 -- N decreases from 15.00 mg/L to 1.84 mg/L with a reduction efficiency of 87.76%, and a removal rate of TN reaches 87.47%. At 39 h, a concentration of NO3-N is 1.51 mg/L, indicating a removal efficiency of 89.92%, and a TN concentration is 1.59 mg/L, indicating a maximum removal rate of TN is 89.40%. In addition, a maximum accumulated concentration of $NO_2$—N occurs at 15th hour of strain culture, which is a logarithmic phase of the strain, and the concentration is 1.31 mg/L. With the further extension of a cultivation time, a concentration of $NO_2$—N gradually decreases until becoming zero at 21 h. There is no accumulation of $NH_{4^+}$—N throughout the cultivation process. In summary, the strain can utilize $NO_3$—N and exhibit denitrification performance while growing, and allows a nitrogen removal rate of 89%, indicating that the strain has an excellent aerobic denitrification ability. The above analysis indicates that the aerobic denitrifying fungus has a huge potential in the degradation of nitrogen. These results show that the aerobic denitrifying fungus *Trichoderma Virens* D4 can make full use of nitrogen sources.

Figure 4:
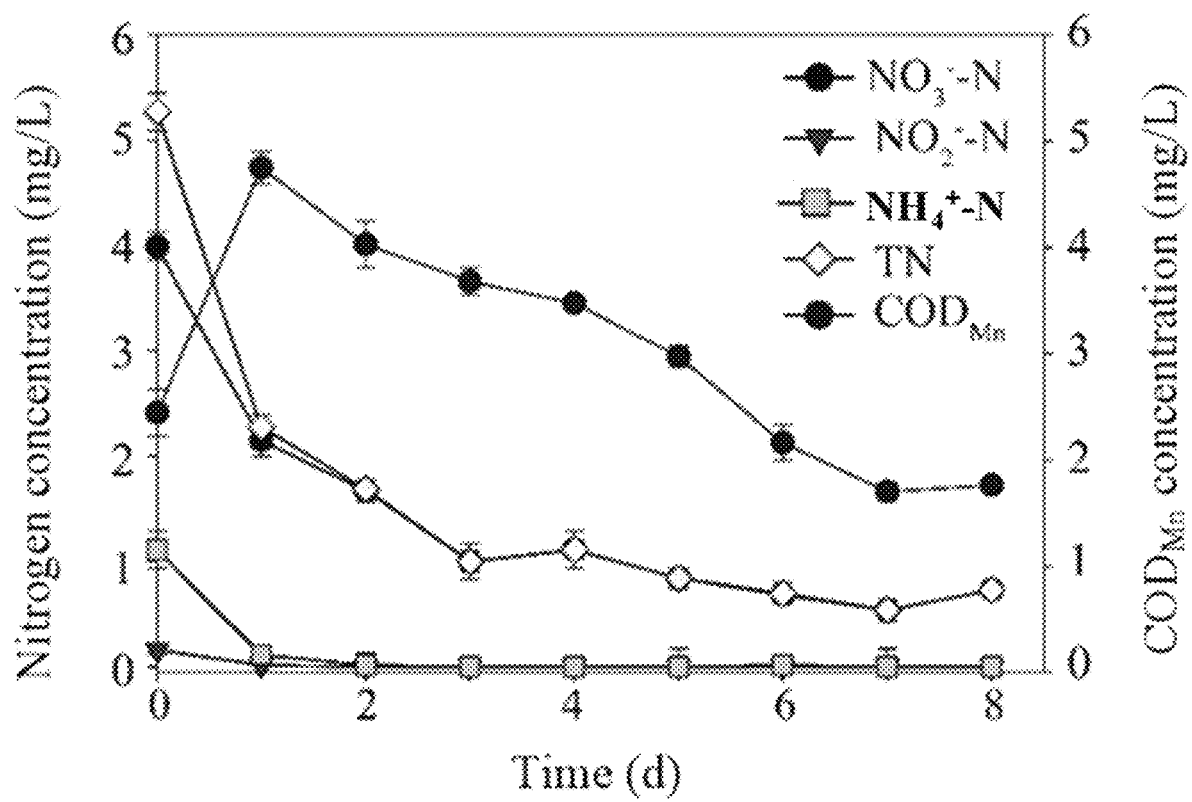
FIG. 4 shows denitrification and decarburization effects of the aerobic denitrifying fungus Trichoderma Virens D4 in the present disclosure for a lake in a city.

Experiment 3: Use of the aerobic denitrifying fungus in raw water with a low carbon-to-nitrogen ratio The strain Trichoderma Virens D4 was inoculated into raw water of an urban river to evaluate the carbon and nitrogen removal performance of the strain Trichoderma Virens D4. The raw water has a TN concentration of 5.27 mg/L and belongs to a water body with a low carbon-to-nitrogen ratio. FIG. 4 shows the denitrification and organic matter degradation of the strain inoculated in the raw water. In the raw water, a concentration of $NO_3$—N is 3.99 mg/L, a concentration of $NO_2$—N is 0.15 mg/L, a concentration of $NH_4^+$—N is 1.11 mg/L, a concentration of TN is 5.27 mg/L, and a concentration of chemical oxygen demand (COD) is 2.44 mg/L. After the strain is inoculated into the raw water, the nitrogen and COD concentrations in the raw water decrease significantly. A removal rate of $NO_3$—N reaches a maximum value of 86.56% and a concentration of $NO_3$—N decreases to 0.54 mg/L on day 7, NO2-N is completely removed on day 2, $NH_4^+$—N is completely removed on day 3, and a removal rate of TN reaches a maximum value of 89.73% and a concentration of TN is 0.54 mg/L on day 7. After the strain is inoculated into the raw water, the COD concentration first increases slightly to 4.75 mg/L, and with the extension of an aeration time, the COD concentration gradually decreases and is stabilized at 1.7 mg/L on day 7, reaching a maximum removal rate of 30.33%.

Further, in order to investigate a potential application of the strain Trichoderma Virens D4 in raw water, the strain was inoculated in a beaker filled with 2 L of raw water with a low carbon-to-nitrogen ratio, a dissolved oxygen concentration was maintained at 7.0 mg/L to 8.5 mg/L by an oxygenation pump, and then a denitrification ability of the strain was investigated. Raw water was collected from a drinking water reservoir in the Xi'an city and tested within 1 h. The strain was inoculated into natural water (v/v=1:9) in a 2 L beaker as a system 1. A dissolved oxygen concentration of this system was maintained at 7.5 mg/L for 9 d. A sample was collected every 24 h and tested by an ultraviolet-visible spectrophotometer to determine the concentrations of ammonia nitrogen ($NH_4^+$—N), nitrate nitrogen ($NO_3$—N), nitrites ($NO_3$—N), total dissolved nitrogen (TDN), and $COD_{Mn}$ in the system.

In the above experiment, the determination and analysis methods of $NH_4^+$—N, $NO_3$—N, $NO_2$—N, and TN all refer to national standards, where a determination and analysis method of $NH_4$—N is based on the "*Water Quality— Ammonia Nitrogen Determination—Nessler's Reagent Spectrophotometry*", a determination and analysis method of $NO_3$—N is based on "*Water Quality—Nitrate Nitrogen Determination—Ultraviolet-Visible Spectrophotometry*", a determination and analysis method of $NO_2$—N is based on "*Water Quality—Nitrite Nitrogen Determination—Ultraviolet-Visible Spectrophotometry*", and a determination and analysis method of TN is based on "*Water Quality—Total Nitrogen (TN) Determination—Ultraviolet-Visible Spectrophotometry*".

In summary, the aerobic denitrifying fungus Trichoderma Virens D4 has a powerful carbon metabolism pathway and denitrification ability and is suitable for an in-situ treatment of a water body with a low carbon-to-nitrogen ratio, and the aerobic denitrifying fungus can play a powerful role in the degradation of nitrogen and carbon.

What is claimed is:

1. A method for selecting an aerobic denitrifying fungus, comprising:
    treating sediments in a reservoir by an ultrasonic shaking technology, comprising subjecting a mud/water mixture collected from a drinking water reservoir to an ultrasonic treatment to obtain a suspension;
    isolating and purifying fungal strains and diluting the suspension to obtain a diluted suspension;
    coating the diluted suspension on a first fungal solid medium to produce first fungal colonies;
    picking fungal colonies with different shapes, colors, and characteristics from the first fungal solid medium; streaking picked fungal colonies on a second fungal solid medium, incubating a streaked fungal solid medium in a biochemical incubator to produce second colonies; and repeating a streaking process a plurality of times until pure colonies are obtained;
    selecting a fungus with an aerobic denitrification function using a denitrification medium;
    screening the pure colonies obtained after a separation and a purification in the denitrification medium
    selecting a fungus with an aerobic denitrification ability; and
    identifying a selected fungal strain by a gene sequencing technology, and naming an identified fungal strain as Trichoderma Virens D4.

2. The method for selecting the aerobic denitrifying fungus according to claim 1, wherein the first fungal solid medium comprises a dichloran rose-bengal chloramphenicol (DRBC) agar: 5.0 g/L of proteose peptone No. 3, 10.0 g/L of glucose, 1.0 g/L of monopotassium phosphate, 0.002 g/L of dichloran, 0.5 g/L of magnesium sulfate, 0.025 g/L of rose Bengal, 0.1 g/L of chloramphenicol, and 15.0 g/L of agar, and has a pH of 5.6±0.2.

3. The method for selecting the aerobic denitrifying fungus according to claim 1, wherein the pure colonies are screened as follows: picking and inoculating the pure colonies by an inoculation needle into the denitrification medium, or washing colonies growing on a plate with a phosphate buffer and then allowing a screening in the denitrification medium.

4. The method for selecting the aerobic denitrifying fungus according to claim 1, wherein the selected fungal strain is identified by an internal transcribed spacer (ITS) gene sequencing technology.

* * * * *